US006638552B1

(12) United States Patent
Blechl et al.

(10) Patent No.: US 6,638,552 B1
(45) Date of Patent: Oct. 28, 2003

(54) GLUTENIN GENES AND THEIR USES

(75) Inventors: Ann E. Blechl, Albany, CA (US); Olin D. Anderson, Pleasant Hill, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 1125 days.

(21) Appl. No.: 08/785,716

(22) Filed: Jan. 16, 1997

Related U.S. Application Data

(62) Division of application No. 08/586,331, filed on Jan. 16, 1996, now Pat. No. 5,650,558.

(51) Int. Cl.$^7$ ................................................. A21D 2/00

(52) U.S. Cl. ....................... 426/463; 426/622; 530/374; 530/375

(58) Field of Search ............................... 426/463, 622; 530/374, 375

(56) References Cited

U.S. PATENT DOCUMENTS

| | | | | | |
|---|---|---|---|---|---|
| 1,289,883 | A | * | 12/1918 | Olson ......................... | 426/464 |
| 2,797,212 | A | * | 6/1957 | Miley et al. ................ | 426/463 |
| 3,868,355 | A | * | 2/1975 | Rodgers ...................... | 426/463 |
| 4,150,016 | A | * | 4/1979 | Johannson ................... | 426/463 |
| 4,826,765 | A | * | 5/1989 | Greene et al. ................ | 435/68 |
| 5,003,045 | A | | 3/1991 | Hoffman ...................... | 530/378 |
| 5,102,796 | A | | 4/1992 | Hall et al. ................... | 435/172.3 |
| 5,106,739 | A | | 4/1992 | Comai et al. ............... | 435/172.3 |
| 5,180,873 | A | | 1/1993 | Jorgensen ................... | 800/205 |
| 5,278,057 | A | | 1/1994 | Jorgensen ................... | 435/172.3 |
| 5,283,184 | A | | 2/1994 | Jorgensen et al. .......... | 435/172.3 |
| 5,308,635 | A | | 5/1994 | Payne et al. ................. | 426/549 |
| 5,365,016 | A | | 11/1994 | Burrell et al. .............. | 800/205 |
| 5,420,034 | A | | 5/1995 | Kridl et al. ................ | 435/240.4 |

OTHER PUBLICATIONS

Ann E. Blechl, Gale F. Lorens, Frank C. Greene, Bruce E. Mackey, and Olin D. Anderson, "A Transient Assay for Promoter Activity of Wheat Seed Storage Protein Genes and Other Genes Expressed in Developing Endosperm," *Plant Science* 102:69–80 (1994).

O.D. Anderson and F.C. Greene, "The Characterization and Comparative Analysis of High–molecular–weigth Gletenin Genes from Genomes A and B of a Hexaploid Bread Wheat," *Theoretical and Applied Genetics* 77:689–700 (1989).

N.G. Halford J.M. Field, H. Blair, P. Urwin, K. Moore, L. Robert, R. Thompson, R.B. Flavell, A.S. Tatham, and P.R. Shewry, "Analysis of HMW Glutenin Subunits Encoded by Chromosome 1A of Bread Wheat (*Triticum aestivum* L.) Indicates Quantitative Effects on Grin Quality," *Theoretical and Applied Genetics* 83:373–378 (1992).

Ann E. Blechl, J. Troy Weeks, Angie S. Tam, and Olin D. Anderson, "Modification of wheat utilization properties using molecular biology and genetic transformation", 14th ICC Congress, The Hague, Netherlands, Jun. 5–9, 1994, abstract No. L 1.3.

Ann E. Blechl, Olin D. Anderson, J. Troy Weeks, "Biotechnological Approaches to Wheat Improvement", *Cereal foods World* Aug. 1994, 1994 AACC Annual Meeting, abstract No. 226.

F. Bekes, O. Anderson, Gras P.W., Gupta, R.B., A. Tam, C.W. Wrigley, and R. Appels, "The Contributions of Mixing Properties of 1D HMW Glutenin Subunits Express in a Bacterial System," *Improvement of Cereal Quality by Genetic Engineering*, R. Henry and J.A. Ronalds, Eds., Plenum Press, New York, pp. 97–103 (1994).

Olin D. Anderson, Ann E. Blechl, Frank C. Greene, and J. Troy Weeks, "Progress Towards Genetic Engineering of Wheat with Improved Quality," *Improvement of Cereal Quality by Genetic Engineering*, R. Henry and J.A. Ronalds, Eds., Plenum Press, New York, pp. 87–95, (1994).

Olin D. Anderson, Frank C. Greene, Ryan e. Yip, Nigel G. Halford, Peter R. Shewry and J.–M. Malpica–Romero, "Nucleotide Sequences of the Two High–molecular–weight Glutenin Genes fromthe D–genome of a Hexaploid Bread Wheat, *Triticum aestivum* L. cv Cheyenne," *Nucleic Acids Research* 17:461–462 (1989).

F. MacRitchie, "Physicochemical Properties of Wheat Proteins in Relation to Functionality," *Advances in Food and Nutrition Research* 36:1–87 (1992).

G.J. Lawrence, F. Macritchie and C.W. Wrigley, "Dough and Baking Quality of Wheat Lines Deficiencient in Glutenin Subunits Controlled by the Glu–A1, Glu–B1 and Glu–D1 Loci," *Jouranl of Cereal Science* 7:109–112 (1988).

P.R. Shewry, N.G. Halford, and A.S. Tatham, "High Molecular Weigth Subunits of Wheat Glutenin," *Journal of Cereal Science* 15:105–120 (1992).

F. Bekes, P.W. Gras, R.B. Gupta, D.R. Hickman, and A.S. Tatham,, "Effects of a High $M_r$ Glutenin Subunit (1B×20) on the Dough Mixing Properties of Wheat Flour," *Journal of Cereal Science* 19:3–7 (1994).

V. Colot, L.S. Robert, T.A. Kavanagh, M.W. Bevan and R.D. Thompson, "Localization of Sequences in Wheat Endosperm Protein Genes which Confer Tissue–specific Expression in Tobacco," *The EMBO Journal* 6:3559–3564 (1987).

Arun P. Aryan, G. An and Thomas W. Okita, "Structural and Functional Analysis of Promoter from Gliadin, and Endosperm–specific Storage Protein Gene of *Triticum aestivum* L.," *Mol. Gen. Genet.* 225:65–71 (1991).

(List continued on next page.)

Primary Examiner—Michael P. Woodward
(74) *Attorney, Agent, or Firm*—Margaret A. Connor; John Fado

(57) ABSTRACT

The present invention is directed to methods of improving flour by altering glutenin content in seeds of plants, particularly wheat. The invention relates to methods of introducing a recombinant construct comprising a glutenin gene into a parental plant.

1 Claim, 3 Drawing Sheets

OTHER PUBLICATIONS

Pilar Barcelo, Christine Hagel, Dirk Becker, Antonio Martin and Horst Lorz, "Transgenic Cereal (tritordeum) Plants Obtained at High Efficiency by Microprojectile Bombardment of Inflorescence Tissue," *The Plant Journal* 5:583–592 (1994).

J. Troy Weeks, Olin D. Anderson, and Ann E. Blechl, "Rapid Production of Multiple Independent Lines of Fertile Transgenic Wheat (*triticum aestivum*)," *Plant Physiol.* 102:1077–1084 (1993).

Maria–Jesus Cornejo, Virginia L. Wong, and Ann E. Blechl, "Cryopreserved callus: a source of protoplasts for rice transformation," *Plant Cell Reports* 14:210–214 (1995).

Peter I. Payne, "Genetics of Wheat Storage Proteins and the Effect of Allelic Variation on Bead–Making Quality," *Ann. Rev. Plant Physiol.* 38:141–143 (1987).

G. Galili, "Heterologous Expression of a Wheat High Molecular Weight Glutenin Gene in *Escherichia coli,*" *Proc. Natl. Acad. Sci. USA* 86:7756–7760 (1989).

* cited by examiner

GLUTENIN GENES AND THEIR USES

This application is a division of application Ser. No. 08/586,331, filed Jan. 16, 1996, now U.S. Pat. No. 5,650,558.

FIELD OF THE INVENTION

The present invention relates generally to plant molecular biology. In particular, it relates to nucleic acids and methods for improving glutenin content of plants.

BACKGROUND OF THE INVENTION

The glutenins, which include both high molecular weight (HMW) glutenin subunits and low molecular weight (LMW) glutenin subunits, comprise an economically important class of wheat seed storage proteins. The apparent molecular weights of the individual HMW glutenin polypeptides or subunits range from 90 to 200 kDa. These subunits crosslink by disulfide bonds among themselves and with LMW glutenin polypeptides to form polymers exceeding one million daltons in molecular weight. HMW glutenins constitute 8–10%, while LMW glutenins constitute 15–20% of the total endosperm protein. Both HMW and LMW glutenin proteins play important functional roles in determining the end-uses of wheat flour.

In wheat, HMW glutenins are encoded at the Glu-1 loci on the long arms of the group 1 chromosomes. Each locus consists of two separate genes, encoding an x-type and a y-type subunit, respectively. These pairs have never been confirmed to be separated by recombination. This has made determination of their separate contributions to bread dough properties difficult to assess by genetic correlation studies. For a review of the genetics and biochemistry of glutenin polypeptides, see, Shewry et al., *J. Cereal Sci.* 15:105–120 (1992).

Both the quantity and identity of specific HMW glutenin alleles contribute to the differences in bread-making quality of various cultivars. For instance, deletion of glutenin genes results in a decrease in the overall levels of HMW glutenins, which results in decreases in bread-making quality (see, e.g., Lawrence et al. *J. Cereal Sci* 7:109–112 (1988)).

The effects of overproducing HMW glutenin on protein accumulation and baking quality has not been assessed because such lines of wheat have not been found among natural populations. In addition, direct alteration of the glutenin subunits that form the polymers is not possible using standard breeding methods. Thus, the art lacks reproducible and efficient methods of producing lines with altered glutenin contents. The present invention addresses these and other needs.

SUMMARY OF THE INVENTION

The present invention provides methods of increasing glutenin in the endosperm of wheat plants. The methods and plants of the invention therefore are useful in providing flour and dough having improved end-use properties. The methods comprise introducing into a parental wheat plant a recombinant expression cassette comprising a nucleic acid encoding a glutenin polypeptide and selecting progeny wheat plant having increased glutenin content in the endosperm of mature seed. The glutenin content of the progeny is preferably at least about 15% greater than the glutenin of the parental wheat plant.

Any method of introducing the expression cassette into the parental plant can be used. Particle bombardment is a convenient method for producing transgenic plants. Once the expression cassette is stably integrated into the genome, standard sexual crosses can be used to introduce the expression cassette into desired lines.

In some embodiments, the nucleic acid introduced into the plant encodes a chimeric glutenin polypeptide. For instance, the chimeric polypeptide may comprise sequences from an x-type glutenin polypeptide and a y-type glutenin polypeptide. Exemplary genes for this purpose include the Glu-D1-1b gene and the Glu-D1-2b gene.

The expression cassette may further comprise a seed-specific promoter to direct expression of the introduced nucleic acid to the endosperm. A convenient promoter for this purpose is the promoter from the Glu-D1-2b gene.

Any wheat cultivar can be used as the parental line in the present invention. An exemplary cultivar is Bobwhite.

The invention also provides wheat plants comprising a recombinant expression cassette comprising a nucleic acid encoding a glutenin polypeptide. The plants of the invention have a glutenin content in the endosperm of a mature seed at least about 15% greater than the glutenin content in the endosperm of a mature seed from a parental wheat plant. The percentage of total endosperm protein which is glutenin will usually depend upon the glutenin content of the parental line. Usually, HMW glutenins account for at least about 15% of the total protein in the endosperm of the mature seed from plants of the invention.

The invention further provides recombinant constructs comprising a wheat glutenin gene promoter of about 400 to about 2800 nucleotides operably linked to a heterologous polynucleotide sequence. These constructs are particularly useful in directing expression of the heterologous sequence to seeds of transgenic plants. An exemplary wheat glutenin gene from which the promoters of the invention can be derived is Glu-D1-2b.

Definitions

The term "plant" includes whole plants, plant organs (e.g., leaves, stems, roots, flowers, etc.), seeds and plant cells and progeny of same. The class of plants which can be used in the methods of the invention is generally as broad as the class of higher plants amenable to transformation techniques, including both monocotyledonous and dicotyledonous plants.

A "heterologous sequence" is one that originates from a foreign species, or, if from the same species, is substantially modified from its original form. For example, a promoter operably linked to a heterologous structural gene is from a species different from that from which the structural gene was derived, or, if from the same species, one or both are substantially modified from their original form.

A "glutenin polypeptide" is a gene product of a glutenin gene or glutenin polynucleotide sequence. A glutenin polypeptide can be either a LMW glutenin or a HMW glutenin. A glutenin polypeptide contains cysteine residues by which disulfide bonds are formed with other glutenin polypeptides to form polymers. The composition and size of the repeat region is also important to polymer formation.

A "chimeric glutenin polypeptide" is glutenin gene product that comprises a modified amino acid sequence. Modifications, as explained in detail below, can be in the form of substitutions, deletions, or additions of single amino acids or groups of amino acids. Thus, chimeric glutenin polypeptides can be hybrid glutenin polypeptides comprising sequences from two or more different subunits or may be polypeptides in which single amino acid modifications are made.

In the case where an inserted polynucleotide sequence is transcribed and translated to produce a functional glutenin polypeptide, one of skill will recognize that because of codon degeneracy, a number of polynucleotide sequences will encode the same polypeptide. These variants are specifically covered by the terms "glutenin gene" or "glutenin polynucleotide sequence". In addition, the terms specifically include those full length sequences substantially identical (determined as described below) with a glutenin gene sequence and that encode proteins that retain the function of the glutenin polypeptide. Thus, in the case of wheat glutenin genes disclosed here, the term includes variant polynucleotide sequences which have substantial identity with the sequences disclosed here and which encode glutenin polypeptides capable of crosslinking by disulfide bonds with other glutenin polypeptides to form glutenin polymers.

Two polynucleotides or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a segment or "comparison window" to identify and compare local regions of sequence similarity. Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85:2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis., or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other under stringent conditions. Stringent conditions are sequence dependent and will be different in different circumstances. Generally, stringent conditions are selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code.

DESCRIPTION OF THE PREFERRED EMBODIMENTS

This invention relates to plant glutenin genes, in particular wheat glutenin genes. Nucleic acid sequences from glutenin genes can be used to modify glutenin content in transgenic plants, in particular wheat plants. In addition, the invention provides new seed-specific promoters useful for directing expression of desired genes in a number of plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

Glutenin Polypeptides and Genes

Figure 1:
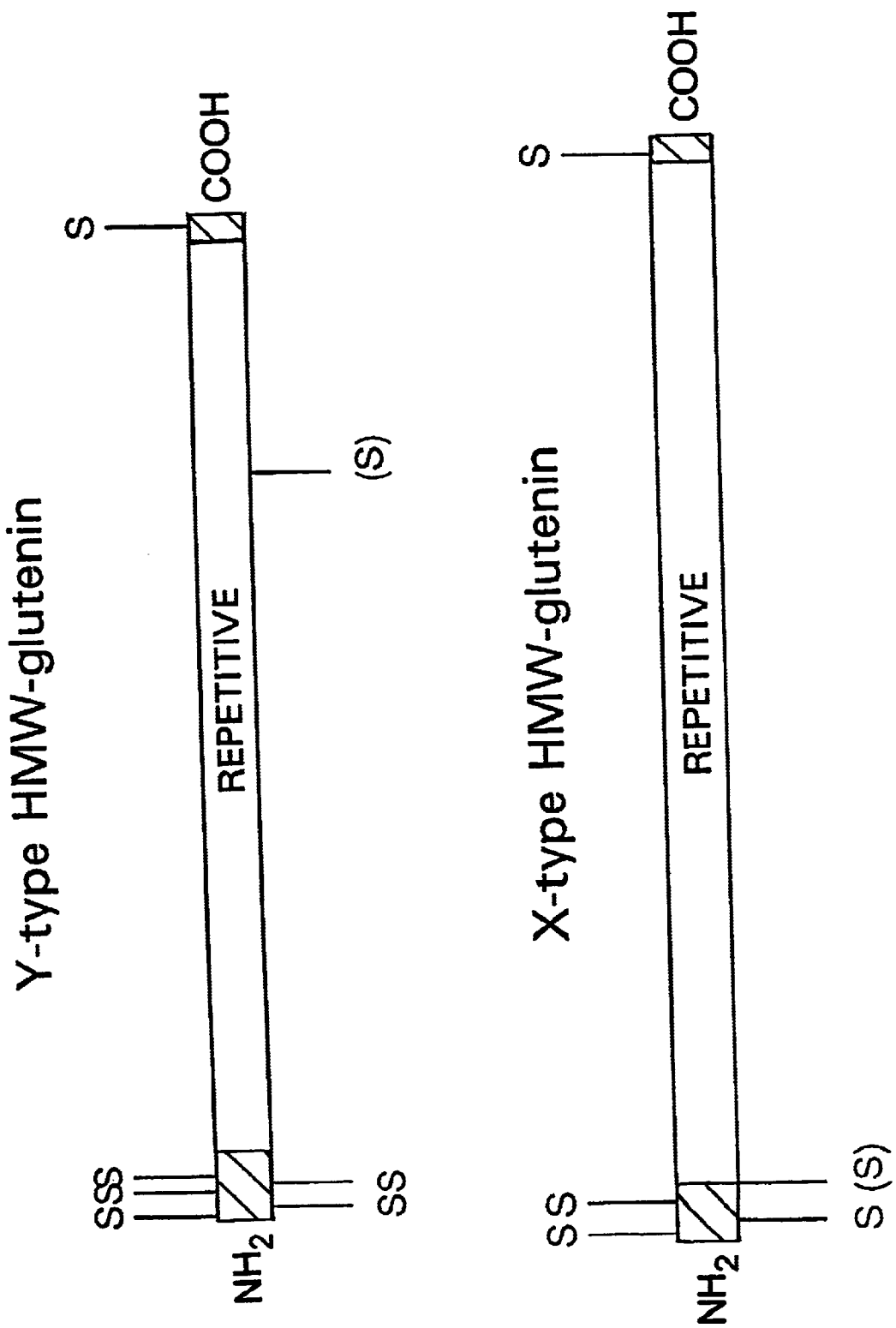
FIG. 1 is a diagram showing the domains of y-type and x-type HMW glutenins. The C- and N-terminal domains are shaded, the locations of cysteine residues are designated by S.

The HMW glutenins are composed primarily of a central domain of 45–90 repeating two or three simple motifs, comprising chiefly glutamine and proline. This unusual primary structure results in a rod-like secondary structure as assessed by circular dichroism and SEM. Cysteines in the C- and N-terminal domains of the molecules are known to be critical for the formation of intermolecular disulfide bonds (FIG. 1). The quaternary interactions of these proteins are of interest because the disulfide crosslinks among HMW and LMW subunits is thought to be integral to the elastic properties of dough.

Any isolated glutenin gene can be used in the present invention. The particular polynucleotide sequence used is not a critical feature of the invention, so long as the desired alteration in glutenin content is achieved. As noted above, HMW glutenins (both x-types and y-types) are encoded at the Glu-1 locus. In hexaploid wheat the group 1 chromosomes are designated 1A, 1B and 1D. Studies of the frequency of alleles at each of the loci indicate the presence of at least three alleles at Glu-A1, 11 alleles at Glu-B1, and six alleles at Glu-D1. The gene products of each allele are designated by noting the chromosome, followed by its classification as x or y, and a number (see, MacRitchie, *Advances in Food and Nutrition Research* 36:1–87 (1992)).

Wheat HMW glutenin genes have been cloned and described in the literature. For instance, a complete set of HMW glutenin genes have been isolated and sequenced from the hard red winter wheat Cheyenne (Anderson et al. *Wheat Genetics Symposium* Proc. pp 699–704 (Bath Press, Cambridge, UK, 1988), including two, Dx5 and Dy10, with the highest correlation with good flour quality (Anderson et al. *Nuc. Acids. Res.* 17:461–462 (1989)). Other particularly useful HMW glutenins include Ax and Bx alleles.

The isolation of other glutenin genes may be accomplished by a number of techniques. For instance, oligonucleotide probes based on the sequences disclosed in the prior art can be used to isolate the desired gene from a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from endosperm and a cDNA library which contains the glutenin gene transcript is prepared from the mRNA.

Alternatively, the nucleic acids of interest can be amplified from nucleic acid samples using amplification techniques. For instance, polymerase chain reaction (PCR) technology to amplify the sequences of the glutenin and related genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: *A Guide to Methods and Applications*. (Innis, M, Gelfand, D., Sninsky, J. and White, T., eds., *Academic Press*, San Diego (1990)).

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Isolated sequences prepared as described herein can then be used to modify glutenin gene expression and therefore glutenin content in plants. One of skill will recognize that the nucleic acid encoding a functional glutenin protein need not have a sequence identical to the exemplified genes disclosed here. Thus, genes encoding chimeric glutenin polypeptides can be used in the present invention.

As noted above, glutenin polypeptides, like other proteins, have different domains which perform different functions. Thus, the glutenin gene sequences need not be full length, so long as the desired functional domains of the protein is expressed. Chimeric glutenin polypeptides can be readily designed utilizing various recombinant DNA techniques well known to those skilled in the art. For example, the chains can vary from the naturally occurring sequence at the primary structure level by amino acid substitutions, additions, deletions, and the like. In particular, cysteine residues may be added, deleted or moved within the polypeptide to achieve a modified glutenin polypeptide with desired properties. Chimeric polypeptides may also be produced by fusing coding sequences from two or more glutenin genes. All of these modifications can be used in a number of combinations to produce the final modified protein chain.

Preparation of Recombinant Constructs

To use isolated glutenin sequences in modifying glutenin content in plants, recombinant DNA vectors suitable for transformation of plant cells are prepared. A DNA sequence coding for the desired glutenin polypeptide, for example a cDNA or a genomic sequence encoding a full length protein, is conveniently used to construct a recombinant expression cassette which can be introduced into the desired plant. An expression cassette will typically comprise the glutenin polynucleotide sequence operably linked to a promoter sequence and other transcriptional and translational initiation regulatory sequences which will direct the transcription of the sequence from the glutenin gene in the intended tissues (e.g., endosperm) of the transformed plant.

For example, a constitutive plant promoter fragment may be employed which will direct expression of the glutenin in all tissues of a plant. Such promoters are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may be under environmental control.

Such promoters are referred to here as "inducible" promoters. Examples of environmental conditions that may effect transcription by inducible promoters include pathogen attack, anaerobic conditions, or the presence of light.

Typically, the promoters used in the constructs of the invention will be "tissue-specific" and are under developmental control such that the desired gene is expressed only in certain tissues, such as leaves, roots, fruit, seeds, or flowers. Promoters that direct expression in seeds, particularly the endosperm are particularly preferred. Examples of such promoters include the promoter from genes encoding seed storage proteins, such as napin, cruciferin, phaseolin, and the like (see, U.S. Pat. No. 5,420,034). Other promoters suitable for expressing glutenin genes in cereals include promoters from genes encoding gliadins, cereal prolamines (e.g., zein, hordein, secalin, and avenin) and starch biosynthetic enzymes.

The endogenous promoters from glutenin genes are particularly useful for directing expression of glutenin genes to the seed, particularly the endosperm. These seed-specific promoters can also be used to direct expression of heterologous structural genes. Thus, the promoters can be used in recombinant expression cassettes to drive expression of any gene whose expression in seeds is desirable. Examples include genes encoding proteins useful in increasing the nutritional value of seeds (e.g., genes encoding proteins involved in lipid, protein, and carbohydrate or starch biosynthesis). Other genes include those encoding pharmaceutically useful compounds, and genes encoding plant resistance products to combat fungal or other infections of the seed.

The glutenin promoters can also be used to initiate transcription of mRNA molecules to inhibit expression of an endogenous endosperm gene. Exemplary genes whose expression could be inhibited include genes encoding glutenins, enzymes involved in carbohydrate or lipid synthesis, secalins, and the like. Means for inhibiting gene expression in plants using recombinant DNA techniques are well known. For instance, antisense technology can be conveniently used. see, e.g., Sheehy et al., *Proc. Nat. Acad. Sci. USA,* 85:8805–8809 (1988), and Hiatt et al., U.S. Pat. No. 4,801,340. Catalytic RNA molecules or ribozymes can also be used to inhibit expression of endosperm-specific genes. The design and use of target RNA-specific ribozymes is described in Haseloff et al. *Nature,* 334:585–591 (1988). Introduction of nucleic acid configured in the sense orientation has also been shown to be an effective means by which to block the transcription of target genes. For an example of the use of sense suppression to modulate expression of endogenous genes see, Napoli et al., *The Plant Cell* 2:279–289 (1990), and U.S. Pat. Nos. 5,034,323, 5,231,020, and 5,283,184.

The glutenin promoters of the invention are typically at least about 400 base pairs in length, and often at least about 800 or about 1000 base pairs. The length of the promoters is typically less than about 3500 base pairs, usually less than about 2800 base pairs and often less than about 2000 base pairs in length. The length of the promoters is counted upstream from the translation start codon of the native gene. One of skill will recognize that use of the "about" to refer to lengths of nucleic acid fragments is meant to include fragments of various lengths that do not vary significantly from the lengths recited here and still maintain the functions of the claimed promoters (i.e., seed-specific gene expression).

To identify glutenin promoters, the 5' portions of a genomic glutenin gene clone is analyzed for sequences characteristic of promoter sequences. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) N G. J. Messing et al., in *Genetic Engineering in Plants,* pp. 221–227 (Kosage, Meredith and Hollaender, eds. 1983).

In preparing expression vectors of the invention, sequences other than the promoter and the structural gene of interest are also preferably used. If proper polypeptide expression is desired, a polyadenylation region at the 3'-end of the glutenin coding region should be included. The polyadenylation region can be derived from the natural gene, from a variety of other plant genes, or from T-DNA.

The vector comprising the sequences from a glutenin gene will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon, or phosphinothricin (the active ingredient in bialaphos and Basta).

Preparation of Transgenic Plants

The DNA constructs described above may be introduced into the genome of the desired plant host by a variety of conventional techniques. Techniques for transforming a wide variety of higher plant species are well known and described in the technical and scientific literature. See, for example, Weising et al., *Ann. Rev. Genet.* 22:421–477 (1988).

The DNA construct may be introduced directly into the genomic DNA of the plant cell using techniques such as biollistic methods, electroporation, PEG poration, and microinjection of plant cell protoplasts or embryogenic callus. Alternatively, the DNA constructs may be combined with suitable T-DNA flanking regions and introduced using an *Agrobacterium tumefaciens* or *A. rhizogenes* vector.

Particle bombardment techniques are described in Klein et al., *Nature* 327:70–73 (1987). A particularly preferred method of transforming wheat and other cereals is the bombardment of calli derived from immature embryos as described by Weeks et al. *Plant Physiol.* 102:1077–1084 (1993).

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Nat. Acad. Sci. USA* 82:5824 (1985).

*Agrobacterium tumefaciens*-meditated transformation techniques are also well described in the scientific literature. See, for example Horsch et al. *Science* 233:496–498 (1984), and Fraley et al. *Proc. Natl. Acad. Sci. USA* 80:4803 (1983). Although Agrobacterium is useful primarily in dicots, certain monocots can be transformed by Agrobacterium. For instance, Agrobacterium transformation of rice is described by Hiei et al. i Plant J. 6:271–282 (1994).

The present invention is particularly useful in wheat and other cereals. A number of methods of transforming cereals have been described in the literature. For instance, transformation of rice is described by Toriyama et al. *Bio/Technology* 6:1072–1074 (1988), Zhang et al. *Theor. Appl. Gen.* 76:835–840 (1988), and Shimamoto et al. *Nature* 338:274–276 (1989). Transgenic maize regenerants have been described by Fromm et al., *Bio/Technology* 8:833–839 (1990) and Gordon-Kamm et al., *Plant Cell* 2:603–618 (1990)). Similarly, oats (Sommers et al., *Bio/Technology* 10:1589–1594 (1992)), wheat (Vasil et al., *Bio/Technology* 10:667–674 (1992)); Weeks et al., *Plant Physiol.* 102:1077–1084 (1993)), sorghum (Casas et al., *Proc. Natl. Acad. Sci. USA* 90:11212–11216 (1993)), rice (Li et al., *Plant Cell Rep.* 12:250–255 (1993)), barley (Yuechun and Lemaux, *Plant Physiol.* 104:37–48 (1994)), and rye (Castillo et al., *Bio/Technology* 12:1366–1371 (1994)) have been transformed via bombardment.

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the glutenin polynucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The methods of the present invention are particularly useful for incorporating the glutenin polynucleotides into transformed plants in ways and under circumstances which are not found naturally. In particular, the glutenin polypeptides may be expressed at times or in quantities which are not characteristic of natural plants.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The invention has use over a broad range of types of plants. The glutenin genes are preferably expressed in cereal species commonly used for production of flour, e.g., wheat, rye, oats, and the like.

The seed-specific promoters from glutenin genes can be used in essentially any plant species. For instance, the promoters or genes described here can be used in species from the genera Asparagus, Atropa, Avena, Brassica, Citrus, Citrullus, Capsicum, Cucumis, Cucurbita, Daucus, Fragaria, Glycine, Gossypium, Helianthus, Heterocallis, Hordeun, Hyoscyamus, Juglans, Lactuca, Linum, Loliun, Lycopersicon, Malus, Manihot, Majorana, Medicago, Nicotiana, Oryza, Paniewn, Pannesetum, Persea, Phaseolus, Pisum, Pyrus, Prunus, Raphanus, Secale, Senecio, Sinapis, Solanum, Sorghum, Trigonella, Triticum, Vitis, Vigna, and, Zea. Plants that are particularly useful in the invention include Avena, Brassica, Glycine, Hordeum, Oryza, Phaseolus, Pisum, Secale, Sorghum, Triticum, Wgna, and Zea.

As noted above, the invention is particularly useful for improvement of wheat cultivars. Any wheat cultivar may be improved by the methods of the invention. Exemplary lines include hexaploid lines such as Anza, Shasta, Yecoro Rojo, Siouxland, Freedom, Tam107, and Tam200.

The effect of the modification of glutenin gene expression can be measured by detection of increases or decreases in desired glutenin protein levels using, for instance, gel electrophoresis, as described below. Quantification of HMW glutenin content can be carried out by SDS/PAGE densitometry, as described below.

Other methods for quantifying glutenin content include sonication of flour dispersions in SDS buffer to solubilize glutenin and other relatively insoluble proteins (see, Singh and MacRitchie in *Wheat End-Use Properties: Wheat and Flour Characterization for Specific End-Uses* H. Salovaara, ed., pp 321–326 (University of Helsinki, Helsinki, 1989). This method is useful in solubilizing at least 95 % of total flour protein. Quantification of the glutenin fraction can then be performed using size exclusion high performance liquid chromatography as described by Batey et al., *Cereal Chem.* 68:207–209 (1991). Other suitable methods include reverse phase HPLC and capillary electrophoresis.

The plants of the invention have increased in glutenin content in the endosperm of mature seeds as compared to the parental lines from which they are derived. The increase is usually at least about 15% as compared to the parental line. More usually, the increase is at least about 20%, preferably at least about 35%, and in more preferred embodiments at least about 45 %. Any of the methods for quantifying glutenins in the endosperm described above can be used to determine the percent increase in glutenin content. A wheat seed typically reaches maturity about 6 to about 10 weeks after anthesis.

Another measure of increased glutenin content in transgenic plants of the invention is glutenin content as a percent of total protein of a mature seed or flour derived from the mature seed. Different wheat cultivars have different glutenin contents as measured using standard methods. Thus, the final glutenin content of the plants of the invention will depend upon the parental line. In the case where HMW glutenin genes are used, the plants of the invention will typically have HMW glutenin contents of at least about 15%, usually at least about 18%, and preferably at least about 20% as measured using standard methods such as those described in detail below.

Analysis of the rheological properties of flour derived from the transgenic plants of the invention can be carried out according to standard physical dough-testing instruments widely used to measure flour and dough quality (see, e.g., MacRitchie, *Advances in Food and Nutrition Research* 36:1–87 (1992)). Such methods include, for instance, use of extensographs to measure tensile strength. Two of the main parameters measured are maximum resistance ($R_{max}$) and extensibility (Ext). Other methods include mixographs and bake-test loaf volume (MacRitchie and Gras *Cereal Chem.* 50:292–302 (1973) as well as SDS-sedimentation tests, amelographs, and cookie spread methods.

The following Examples are offered by way of illustration, not limitation.

EXAMPLE 1

This example demonstrates increase in glutenin content in transgenic wheat plants comprising recombinant constructs of the invention.

Materials and Methods

Construction of the Hybrid HMW Glutenin Expression Plasmid

Figure 2A:
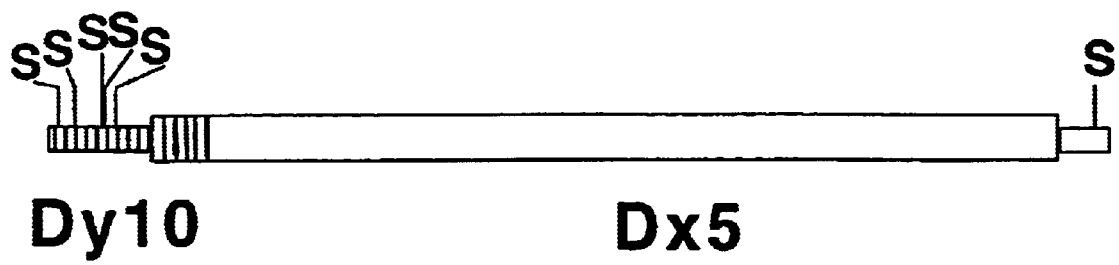
FIG. 2A is a diagram showing the structure of a hybrid glutenin polypeptide of the invention.

Two HMW glutenin subunits, Dx5 and Dy10, encoded by the Glu-D1-1b and Glu-D1-2b genes, respectively, have been most often associated with superior dough strength by genetic correlation studies. A bacterial expression vector comprising a fusion of coding regions of the Dy10 and Dx5 genes is described by Shani et al., *Plant Physiol.* 98:433–441 (1992) . The hybrid HMW glutenin polypeptide encoded by this gene is diagrammed in FIG. 2A.

In this example, the Dy10:Dx5 hybrid coding region was reunited with 5' and 3' flanking sequences from the native Dy10 and Dx5 genes. The construction of a fusion at the HindIII site located at base pairs 429–435 and 385–391 after the A of the start codons of the Glu-D1-2b (Genbank Accession No. X12929) and Glu-D1-1b (Genbank Accession No. X12928) genes (Anderson et al. *Nuc. Acids Res.* 17:461–462 (1989)) and its insertion into the bacterial expression vector pet3A to form pet-3a-10/5 is described by Shani et al., supra.

Thus, the native Dy10 gene provides the promoter, transcription start site, the 5' transcribed untranslated region and the first 145 codons including the 21 amino acid signal peptide. The native Dx5 gene provides its codons 130 to 848 followed by two translation stop codons, the transcription termination and poly(A) addition signals. Because amino acids 138 through 147 are shared by the Dy10 and Dx5 glutenin subunits, the central region of repeating amino acid motifs of the hybrid glutenin polypeptide (thickest boxes in FIG. 2A) is identical to that of Dx5. The configuration of the cysteines (S) and thus of potential disulfide bonds is chimeric in nature: the N-terminal cysteines are of the y-type and the single C-terminal cysteine is typical of x-type subunits.

Figure 2B:
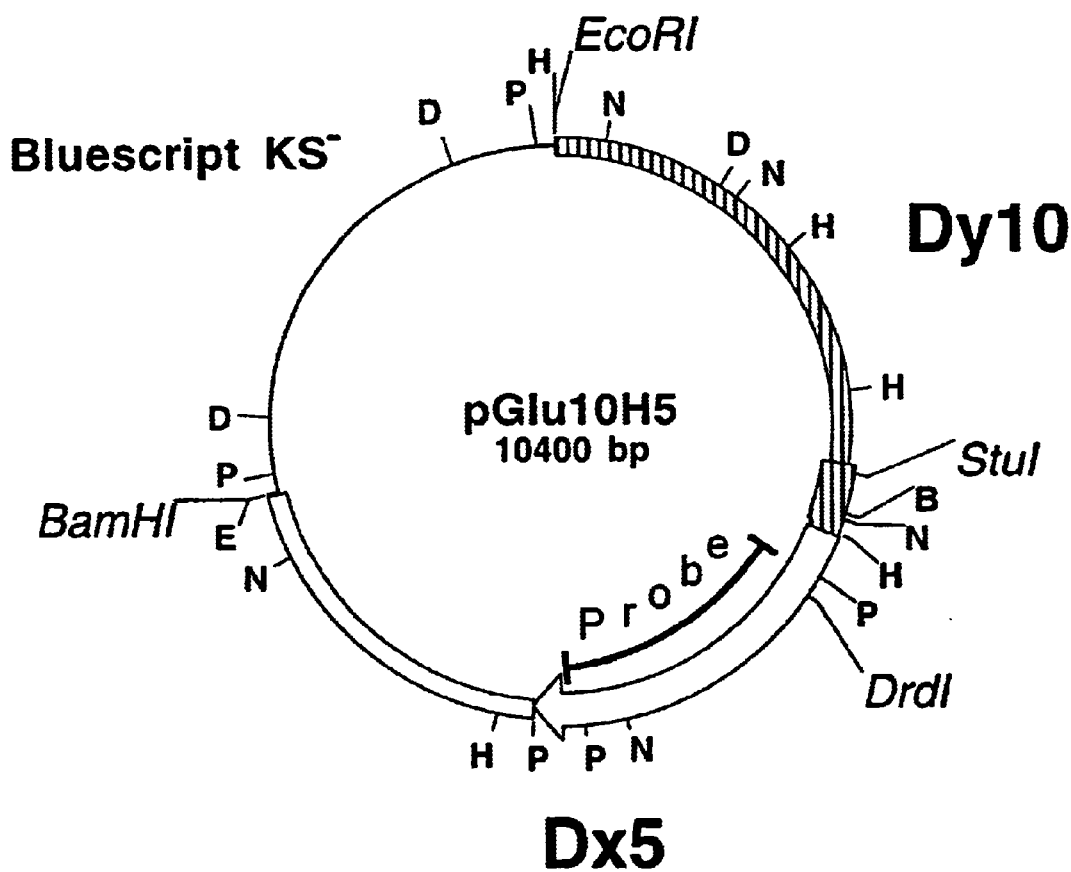
FIG. 2B is a diagram of the recombinant plasmid of the invention which encodes the polypeptide shown in FIG. 2A.

In order to reconstitute the promoter region, transcription start and termination sites, and any other regulatory signals needed for expression in wheat, three fragments were isolated and combined in a single ligation reaction with the Bluescript KS⁻ (Stratagene) vector cut with EcoRI and BamHI: 1) the 715 bp StuI/DrdI fragment that contains the junction region in pET-3a-10/5; 2) the 2800 bp fragment from a clone of the native Dy10 gene beginning at the EcoRI site 5' to the gene and ending at the StuI site 74 bp after the A in the start codon; and 3) the 3800 bp fragment from a clone of the native Dx5 gene that starts at the DrdI site 744 bp after the A in the start codon and ends at a BamHI site in the vector just outside the EcoRI site in the 3' flanking region. A plasmid with the correct structure was identified by restriction analysis and named pGlu10H5 (FIG. 2B). This plasmid was deposited under terms of the Budapest Treaty in the Agricultural Research Culture Collection (NRRL), 1815 North University Street, Peoria, Ill., on Jan. 12, 1996 and has been assigned accession number NRRL B-21517.

The plasmid UBI:BAR which comprises the maize ubiquitin promoter operably linked to the bar gene encoding the enzyme PAT, which inactivates phosphinothricin was prepared as described Cornejo et al. *Plant Mol. Biol.* 23:567–581 (1993).

Both plasmids were prepared by the alkaline lysis method using a Qiagen kit for the final purification. The DNAs were stored in TE buffer at a concentration of 1 mg/ml.

Wheat Transformation 12.5 ug of each DNA (an approximately 2:1 molar ratio of UBI:BAR to pGlu10H5) was coated onto gold particles for bombardment into immature wheat embryos of cultivar Bobwhite essentially as described by Weeks et al. *Plant Physiol.* 102:1077–1084 (1993) except that the embryos were incubated on callus induction media containing mannitol for 4 hours before and 20 hours after bombardment. Transformants were selected on the basis of their resistance to 1 mg/L bialaphos at the callus and green shoot stages of regeneration and to 3 mg/L bialaphos at the rooting stage of regeneration as described by Weeks et al., supra.

Protein Analysis

Protein extracts from immature wheat endosperm were prepared by grinding the tissue or cells in SDS-PAGE sample loading buffer [66 mM Tris pH 6.8, 3% (w/v) SDS, 0.05% (w/v) Bromphenol blue, 2% (v/v) β-mercaptoethanol]. Protein extracts from mature dry wheat seeds were prepared by dissolving flour in sample buffer. SDS-PAGE was according to standard procedures. The separation gels for detection and quantitation of the hybrid subunit were 10% (w/v) acrylamide 0.05% (w/v) bis-acrylamide. The gels were run at 40 mamps constant current until 20 minutes after the bromphenol blue dye front had run off the gel (about 1000 Volt-hours).

The gels were stained by the Neuhoff method with a colloidal suspension of Coomassie blue. Protein standards for molecular weight calibration were purchased from Pharmacia and consisted of Phosphorylase b (94 kDa) Bovine Serum Albumin (67 kDa), Ovalbumin (43 kDa), Carbonic Anhydrase (30 kDa), Soybean Trypsin Inhibitor (20.1 kDa) and α-Lactalbumin (14.4 kDa). Stained gels were scanned using an Alpha Innotech densitometer.

DNA Analysis

Southern analyses of genomic DNA was as described in Weeks et al., supra, except that 10 ug of DNA were loaded into each slot of a 0.6% agarose gel. The probe consisted of the 1578 bp PvuII fragment from the coding region of Dx5 (bracketed in FIG. 2B).

Results

Forty-five independent callus pieces were selected from 4980 embryos bombarded in 10 different experiments; each yielded one to five plants. The $T_0$ primary regenerated plants and the lines derived from them are designated with an unique number following the bombardment number, e.g., plant 126 regenerated from bombardment 7 is 7–126. Plants from twenty-six of these independent line gave rise to progeny embryos that were able to germinate in the presence of 3 mg/L bialaphos when excised from immature seeds three to four weeks after anthesis.

The immature endosperm tissue corresponding to each excised embryo was extracted and screened by SDS-PAGE for the presence of the hybrid glutenin. This SDS-PAGE analysis showed that the migration of the hybrid HMW glutenin subunit is clearly distinguishable from the native HMW subunits under these gel conditions.

Although the lanes did not contain the same amounts of total protein, it was evident that there is variation in the expression levels of the hybrid subunit relative to those of the native HMW subunits in the same seed. Of the twenty-six resistant lines that were derived from co-bombardment experiments including pGlu10OH5, sixteen (60%) lines showed expression of the hybrid subunit in the $T_1$ generation.

Expression Stability

At each successive generation, 24 or 25 immature embryos 3–4 weeks after anthesis were tested for their ability to germinate on bialaphos. Plants were classified as homozygous if all 25 of their progeny embryos exhibited resistance. The levels of transgene expression were assessed in successive generations. In most cases, expression was stable. An apparent increase in expression between the T1 and T2 generations in some plants was explained by the increase in average gene dosage between the heterozygous and homozygous progeny of the T0 plant and T1 generation, respectively. Since the endosperm is triplicate, individual selfed progeny of the To heterozygote could have 0, 1, 2 or 3 copies and the T1 lane contains an average of 8 of these individuals.

In four of the 15 wheat lines analyzed, expression of the hybrid HMW glutenin has not remained at the same levels, but rather has declined as homozygous resistant lines were selected in the $T_2$ or the $T_3$ generations. The decline could be due either to hybrid HMW glutenin transgene inactivation or to loss of unlinked pGlu10H5 transgene(s) copies via segregation.

Cross-linking Ability of the Hybrid Subunit

As noted above, the hybrid HMW glutenin contains a unique configuration of cysteines, y-type at the N-terminus and x-type at the C-terminus. The hybrid HMW glutenin behaved exactly like the native subunits in terms of its solubility in SDS buffers with and without a reducing agent, when examined by SDS-PAGE. The native and hybrid HMW glutenins were partially extracted from both the Bobwhite and the transgenic flours by SDS alone and were present in lower molecular weight polymers. The majority of the hybrid glutenin, however, was insoluble in SDS buffer and could only be extracted when a reducing agent was added. Thus, the configuration of cysteines in the hybrid HMW glutenin does not preclude the formation of either intermolecular disulfide bonds or high molecular weight polymers.

Relative Expression Levels

Figure 3:
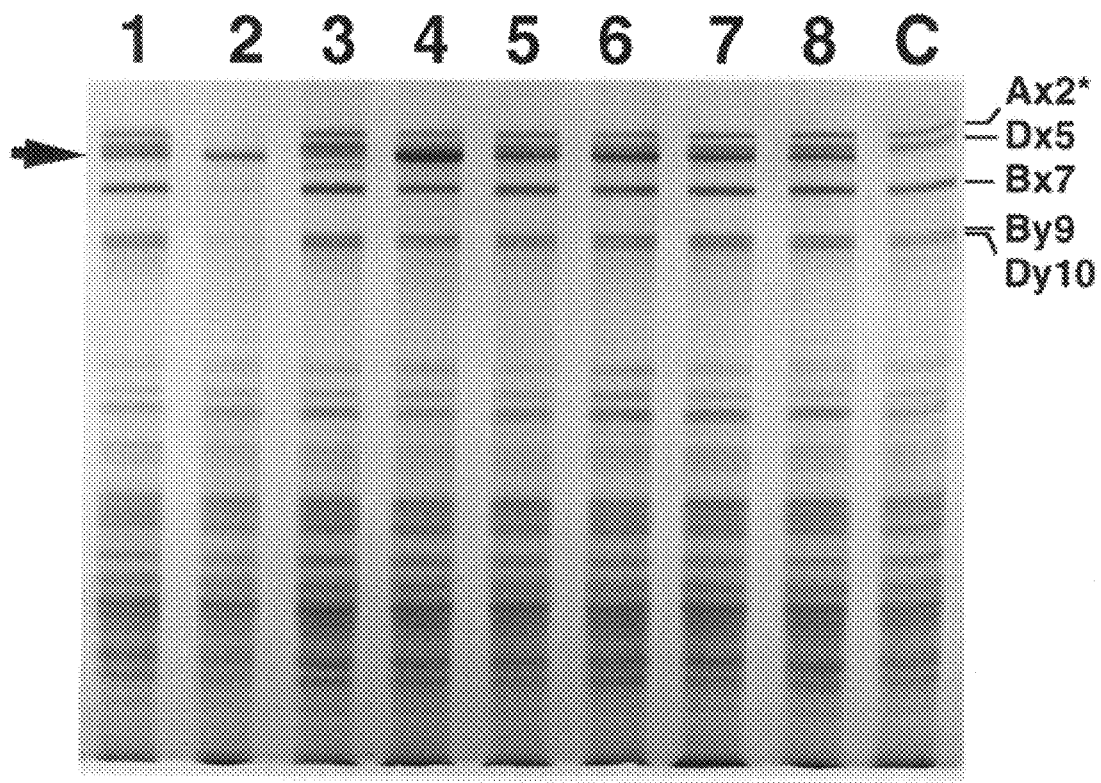
FIG. 3 is photograph of a gel stained with Coomassie blue showing the relative mobility of a hybrid HMW glutenin polypeptide of the invention (marked by the arrow).

FIG. 3 shows SDS-PAGE analysis of protein extracts from eight different transgenic lines (Lanes 1–8) and Bobwhite (C). Each sample was prepared from flour of a mixture of eight mature seeds of a single homozygous $T_2$ or $T_3$ plant. Under these gel conditions, the native By9 and Dy10 subunits are not well resolved and run as a closely spaced doublet of apparent molecular weight 94 kDa. Likewise the two isoforms of the Dx5 subunit are not well-resolved and migrate as a broad band. The Bx7 band is well-separated from other proteins and the darkest of the HMW subunits in intensity. In all the lines except the one shown in Lane 3, the hybrid HMW subunit is present in at least as high a quantity as the native Ax2* (largest) HMW subunit. Thus even a single copy of the hybrid transgene (Lane 1) can support significant expression levels, comparable to those of the native HMW subunits.

In one of the lines (shown in lane 2), synthesis of native HMW glutenin synthesis has declined relative to the other proteins. The extract shown there exhibits reduced synthesis of all the native HMW glutenin compared to the lower molecular weight seed proteins in the same lane.

In order to estimate the levels of the hybrid HMW glutenin relative to those of the native HMW glutenin and other seed proteins, the gel was scanned by densitometry. All the wheat prolamines stay on the gel. However, since proteins of molecular weights less than 33 kDa are run off the gel under the conditions used to separate the hybrid HMW glutenin from the nearby Dx5 subunit band, only relative quantities could be assessed. The results of these comparisons are shown in Table I along with the number of intact transgene copies estimated from restriction enzyme digests of genomic DNA (see below). The hybrid HMW glutenin band constitutes more than 20% of the total HMW glutenins in all the lines except that in lane 3. Thus the transgene has made a significant contribution to the HMW glutenin composition in all the transgenic lines.

In the case where endogenous HMW glutenin accumulation is reduced (Lane 2), the hybrid makes up 62% of the total complement of HMW glutenin. In most lines, the sum of the HMW glutenin accumulation is elevated 29 to 45% relative to the HMW glutenin content of Bobwhite (all sums are normalized to the remainder of the protein their respective lanes). Thus this quantitative analysis suggests that addition of HMW-glutenin gene copies raises the levels of HMW glutenin accumulation in mature seeds.

DNA Analysis

DNA was isolated from the leaves of transgenic plants of each line and assayed for the presence of transgenes by genomic Southern analysis, as described above. Hybridizing bands known to correspond to the transgenes were scanned and their densities compared. The results are shown in Table I. The number ranges from 1 in line 11–291 to about 6 in 14–23 (Table I). This range is much broader than that in total HMW glutenin levels or even hybrid HMW glutenin levels. However the most highly expressing line had one of the highest copy numbers (Line 4) and the poorest expression was in a single copy line (Line 3).

TABLE I

Transgenic HMW-glutenin gene activity in individual wheat lines.

| Line | Transgene Expression | Total HMW subunit as % of total | Gene Copy No. Estimate |
|---|---|---|---|
| 1 | 23% | 135% | 1 |
| 2 | 62% | 70% | 5–6 |
| 3 | 15% | 145% | 1 |
| 4 | 42% | 145% | 4–5 |
| 5 | 23% | 140% | 2 |
| 6 | 24% | 129% | 2 |
| 7 | 22% | 135% | 3–4 |
| 8 | 20% | 143% | 3–4 |

Discussion

The experiments reported here show that levels of HMW glutenins can be increased by addition of gene copies. The behavior of the hybrid subunit is indistinguishable from that of the native subunits. The protein accumulates in the endosperm tissue over the course of seed development and is cross-linked by disulfide bonds into large polymers that cannot be extracted by SDS without addition of reducing agents.

Expression of the hybrid glutenin is under the control of the native Dy10 5' and Dx5 3' flanking sequences. These sequences were sufficient to achieve high levels of the modified seed storage protein. Even a single gene copy supported expression levels comparable to those of the native HMW glutenin genes. Thus, these sequences serve as a source of effective regulatory sequences suitable for expression of other proteins in transgenic wheat and potentially other cereal endosperm.

EXAMPLE 2

This example describes the transformation of wheat using a recombinant construct encoding Dx5 and Dy10.

The recombinant expression vectors were prepared as generally as described above except that the complete Dx5 or Dy10 gene, including 5' and 3' regulatory sequences, were used. The constructs were then introduced into immature wheat embryos by particle bombardment as described above. Analysis of $T_0$ plants and their progeny is performed as described above.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. Wheat flour derived from a plant comprising a recombinant expression cassette comprising a nucleic acid encoding a glutenin polypeptide and a seed-specific promoter, the plant having a glutenin content in the endosperm of a mature seed at least about 30% different than the glutenin content in the endosperm of a mature seed from a parental wheat plant.

* * * * *